United States Patent [19]

Richter et al.

[11]  4,388,473
[45]  Jun. 14, 1983

[54] SUBSTITUTED BENZOIC OR PHENYLACETIC ACID ESTERS HAVING PLANT GROWTH REGULATING PROPERTIES

[75] Inventors: Sidney B. Richter, Fairlawn; Barry Van Gemert, Massillon, both of Ohio

[73] Assignee: PPG Industries, Inc., Pittsburgh, Pa.

[21] Appl. No.: 316,256

[22] Filed: Oct. 29, 1981

[51] Int. Cl.$^3$ .............................................. C07C 69/76
[52] U.S. Cl. ...................................... 560/65; 560/21; 560/47; 71/76; 71/86; 71/105; 71/107
[58] Field of Search ....................... 560/65, 21, 47, 65; 71/76, 86, 105, 107

[56] References Cited

U.S. PATENT DOCUMENTS

| | | | |
|---|---|---|---|
| 3,261,678 | 7/1966 | Searle | 71/2.6 |
| 3,371,107 | 2/1968 | De Gaetano | 260/465 |
| 3,874,939 | 4/1975 | Fraley | 71/111 |
| 4,309,566 | 1/1982 | Konz | 560/65 |

FOREIGN PATENT DOCUMENTS 40-11493 of 1965 Japan ............................. 260/465 D Primary Examiner—Paul J. Killos
Attorney, Agent, or Firm—Edward J. Whitfield

[57] ABSTRACT

This invention relates to substituted benzoic acid or phenylacetic acid ester compounds exhibiting meristematic activity and to the use of such compounds in regulating plant growth.

7 Claims, No Drawings

SUBSTITUTED BENZOIC OR PHENYLACETIC ACID ESTERS HAVING PLANT GROWTH REGULATING PROPERTIES

FIELD OF THE INVENTION

This invention relates to certain substituted benzoic acid or phenylacetic acid esters having plant growth regulating properties and the use of said substituted benzoic acid esters for meristematic control of plant growth.

DESCRIPTION OF THE INVENTION

This invention concerns substituted benzoic acid or phenylacetic acid esters represented by the formula:

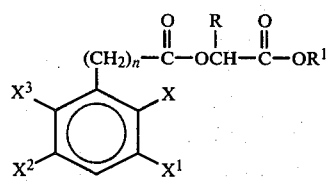

wherein:
X is hydrogen, halogen, or $C_1$ to $C_4$ alkyl or alkoxy;
$X^1$ is hydrogen, halogen, nitro, or

wherein $R^2$ and $R^3$ are the same or different and represent hydrogen, $C_1$ to $C_4$ alkyl, alkoxy or haloalkyl or

wherein $R^4$ is $C_1$ to $C_4$ alkyl;
$X^2$ is halogen or hydrogen;
$X^3$ is hydrogen, halogen, nitro, amino, or $C_1$ to $C_4$ alkyl, alkoxy or haloalkyl, provided that $X^1$ or $X^3$ is other than hydrogen;
R is hydrogen or $C_1$ to $C_6$ alkyl;
$R^1$ is hydrogen, $C_1$ to $C_{10}$ alkyl, haloalkyl or alkoxyalkyl, or an agronomically acceptable ionic species; and
n is 0 or 1.

Exemplary of halogens represented in the above formula are bromine, chlorine, fluorine or iodine, particularly bromine or chlorine. Representative alkyl groups include, for example, methyl, ethyl, n-propyl, isopropyl, n-butyl, isobutyl, tertbutyl, pentyl, heptyl, octyl, isooctyl, nongl or deoyl. Some alkoxy groups that may be mentioned are methoxy, ethoxy, butoxy or octoxy. Methoxymethyl, methoxyethyl and ethoxyethyl are exemplary of suitable alkoxyalkyl groups. As examples of agronomically acceptable ionic species, there may be mentioned alkali metals such as sodium, potassium or lithium; alkaline earth metals such as barium or calcium; ammonium; or alkylammonium or alkanolammonium containing 1 to 4 carbon atoms.

Although any compound within the scope of the above formula is believed to have plant growth regulating properties in accordance with this invention, compounds that have been found especially efficacious are those wherein X and $X^2$ are halogen, e.g., chlorine, and $X^3$ is alkoxy, e.g., methoxy or those wherein X and $X^2$ are halogen, e.g. chlorine and $X^1$ is

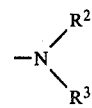

wherein $R^2$ is hydrogen and $R^3$ is

e.g., acetamide. More specifically, the compounds 2,5-dichloro-6-methoxybenzoic acid, (ethoxycarbonyl)ethyl ester and 2,5-dichloro 3-acetamidobenzoic acid, (ethoxycarbonyl)ethyl ester have been found especially efficacious.

It is of course to be understood that the stereo and optical isomers of compounds of the above formula are within the scope of this invention.

The compounds of this invention may be prepared by first halogenating, i.e., chlorinating or brominating, an appropriately substituted benzoic acid or phenyl acetic acid to the corresponding acid halide as follows:

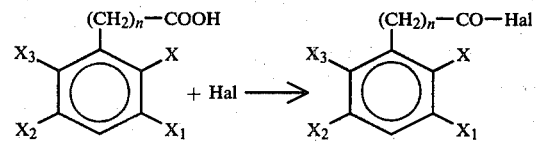

wherein X, $X^1$, $X^2$, $X^3$ and n are as previously defined and Hal is a suitable chlorinating or brominating agent. As examples of chlorinating agents there may be mentioned molecular chlorine, phosphorous trichloride, phosphorous ocydichloride, hydrogen chloride, sulfuryl chloride, phosgene, thionylchloride or hypochlorite compounds. Thionylchloride is particularly preferred. Some examples of brominating agents include molecular bromine, thionylbromide, phosphorous tribromide, potassium bromide, hydrogen bromide or n-bromosuccinimide.

The conversion of the substituted benzoic acid (or substituted phenylacetic acid) to the acid halide is typically conducted in an inert organic liquid solvent, such as for example, hexane, diethyl ether, cyclohexane, heptane, methylene chloride, ethylene dichloride, chloroform, perchloroethylene and the like.

The acid halide is then reacted with an appropriately substituted α-hydroxy carboxylic acid ester in order to form a compound of the invention, as follows:

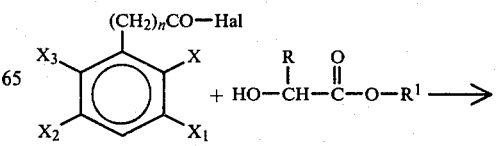

-continued

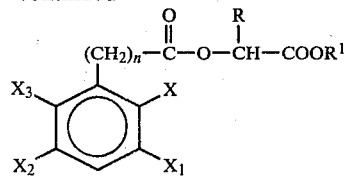

wherein R and $R^1$ are as previously defined. The esterification reaction is typically effected in an inert organic liquid solvent reaction medium of the type previously mentioned and at temperatures ranging from ambient to reflux and usually in the presence of an acid acceptor. Organic tertiary amine type bases are typically employed as acid acceptors, for example, pyridine, 4-dimethylaminopyridine, triethylamine or N,N-dimethylaniline. Inorganic bases such as aqueous sodium hydroxide may, of course, also be used as acid acceptors.

The invention is further illustrated by the following examples.

EXAMPLE I

Preparation of 2,5-dichloro-6-methoxy benzoic acid, (ethoxycarbonyl)ethyl ester (a) The starting material used was a formulation containing the dimethylamine salt of 2,5-dichloro-6-methoxybenzoic acid manufactured by Velsicol Chemical Corporation under the trademark, BANVEL ®.

To isolate the 2,5-dichloro-6-methoxybenzoic acid from other constituents of the BANVEL ® formulation, 250 milliliters of BANVEL ® were treated with aqueous hydrochloric acid to convert the salt to the free acid. Upon acidification, a white precipitate was obtained which was filtered and dried. The precipitate, which contained about 80 percent 2,5-dichloro-6-methoxybenzoic acid was further purified, to wit. To the precipitate was added 250 milliliters of n-propanol and 0.1 gram of p-toluenesulfonic acid. This mixture was charged to a distillation apparatus provided with a Kornblum head and was aceotropically distilled until the head temperature reached 95° C. The mixture was then permitted to reflux until the temperature did not fall below 96° C. The mixture was then stripped of n-propanol in a rotary evaporator and the oily residue was poured into aqueous potassium hydroxide. This mixture was extracted three times with toluene and once with carbon tetrachloride. The aqueous layer was acidified with aqueous hydrochloric acid and the white precipitate formed upon acidification was isolated by vacuum filtration and dried overnight in a vacuum oven. Ten grams of the dried precipitate was recrystallized from 50 milliliters of toluene, affording 8 grams of substantially pure 2,5-dichloro-6-methoxybenzoic acid.

(b) To a 100-milliliter round bottom flask provided with a reflux condenser was charged 20 grams of 2,5-dichloro-6-methoxybenzoic acid (prepared as described in paragraph (a) of this Example) and 30 milliliters (48 grams) of thionyl chloride. The mixture was heated to reflux and maintained at reflux for two hours after which the miture was stripped under vacuum to remove excess thionyl chloride. The oily residue was poured into a separatory funnel along with water and benzene and the contents thoroughly mixed. A small amount of potassium chloride was added to assist phase separation and the benzene layer was washed several times with water. Benzene was then stripped under vacuum and the residue was vacuum distilled. 20.8 grams of a clear oil ws collected, the oil having a boiling point of 82°-84° C. at 0.1 mm Hg. 12 grams of this oil and 75 milliliters of benzene were charged to a 250-milliter round bottom flask provided with a reflux condenser. To this stirred mixture was added, dropwise, 6 milliliters of ethyl lactate and 6 grams of triethylamine in 40 milliliters of benzene. (Some solids formation was noted.) The mixture was then heated to reflux and maintained at reflux for 3½ hours after which the mixture was cooled and filtered, 1.7 grams of amine hydrochloride solids being collected. 5 milliliters of pyridine was added to the filtrate and the mixture was heated to reflux and maintained at reflux overnight. The mixture was then filtered (3.2 grams of amine hydrochloride solids being collected) and the filtrate was washed consecutively with dilute hydrochloric acid, water, dilute aqueous sodium hydroxide and twice more with water. Benzene was then stripped under vacuum leaving a black oil. The oil was vacuum distilled and 6.7 grams of clear oil was collected at 142°-144° C. and 0.2 mm Hg., which oil was identified by NMR spectroscopy as 2,5-dichloro-6-methoxy-benzoic acid, (ethoxycarbonyl)ethyl ester.

EXAMPLE II

Preparation of 2,5-dichloro-3-acetamidobenzoic acid, (ethoxycarbonyl)ethyl ester (a) To a three-necked round bottom flask was charged 20.6 grams (0.1 mole) of 3-amino-2,5-dichloro benzoic acid, 150 milliliters of benzene and 15.8 grams of pyridine. To this dark, blackish-brown solution, was slowly added, with constant stirring, 7.85 grams (0.1 mole) of acetyl chloride in 20 milliliters of benzene over a 30-minute period. A black colored oil layer formed on the bottom of the flask which solidified upon standing for about one-half hour. This solid was broken-up and the mixture was heated at reflux for 30 minutes. The reaction mixture was then poured into aqueous hydrochloric acid/ice and the solid was separated by filtration, washed with water and dried. The solid was then recrystallized from a 2:1 (volume/volume) mixture of water:ethanol, affording, after vacuum drying 15.5 grams of a light tan powder melting at 113° C. to 116° C. and identified as 2,5-dichloro-3-acetamido benzoic acid.

(b) To a 50-milliliter capacity round bottom flask provided with a reflux condenser and a magnetic stirring bar was charged 2.0 grams of 2,5-dichloro-3-acetamido benzoic acid (prepared as described in paragraph (a) of this Example) and 10 milliliters of thionyl chloride. The reaction mixture was heated to reflux and maintained at reflux for 15 minutes after the last observable vestige of solid material had gone into solution. The reaction mixture was then concentrated on a rotary evaporator to remove excess thionylchloride after which 2 milliliters of ethyl lactate, 20 milliliters of benzene and 2 milliliters of pyridine were added. The reaction mixture was heated to reflux, cooled and poured into dilute aqueous hydrochloric acid. About 20 milliliters of benzene was added and the reaction mixture was washed twice with water, twice with dilute aqueous sodium hydroxide and twice again with water after which benzene was stripped by concentration on a rotary evaporator resulting in a viscous, red oil. Petroleum ether was added to the concentrate, in small increments, until a large, solid mass of small crystals were obtained. The crystals were isolated by filtration, washed with petroleum ether and dried affording 1.7 grams of material identified as 2,5-dichloro-3-acetamidobenzoic acid, (ethoxycarbonyl)-ethyl ester.

While the preparations of exemplary compounds of this invention have been described in some detail by the foregoing Examples, it will be understood that any compound within the scope of this invention may be prepared by one skilled in the art, simply by varying the choice of starting materials and by employing the exemplified or other known techniques.

The compounds of this invention, as exemplified by the compounds prepared in the foregoing Examples, were synthesized to determine whether they would exhibit herbicidal activity against common broadleaved and grassy weeds. At application rates of 3 to 5 pounds or more per acre, the compounds did, indeed, exhibit herbicidal activity; but when applied at lower rates, e.g., less than 2 pounds per acre, postemergence, it was surprisingly found that these compounds produced an unexpected response, i.e., plant growth was arrested and it was observed that substantially all meristematic activity had ceased and only nonpolar growth was occuring, which manifested itself by swelling. The already differentiated and fully expanded leaves of the plant remained apparently unharmed. Although younger leaves exhibited some cupping and slight twisting of the leaf petitole, this was not considered to be necessarily epinastic. Moreover, it was observed that expansion of undifferentiated leaves had stopped and no further growth was apparent, although the plant remained healthy and viable. It is theorized that the aforementioned cupping and twisting may have been the result of cell elongation.

A material, such as the compounds of this invention, possessing the type of plant growth regulating activity exhibited, i.e., stopping meristematic growth without distortion of existing or already differentiated plant organs, can be extremely useful. For example, once-over harvesting of crops such as tomatoes, beans, cucumbers, melons, broccoli, brussels sprouts and cauliflower require a plant that flowers, sets, and matures the majority of the fruit so that substantially the entire crop ripens and is ready for harvest at the same time. The compounds of the invention would enable this by stopping or substantially retarding vegetative growth, allowing the plant to start the reproductive phase.

In addition, materials that can stop or retard meristematic growth or cell division could be used to eliminate unwanted seed heads, one example of which would be that of inhibiting sucker growth in tabacco plants. Also, seed head inhibition would be useful in pasture maintenance where seed head formation is particularly undesirable. Since the growing point on grasses is at or near soil level, inhibition of seed head growth can be effected without inhibiting growth of the leaves. Furthermore, growth retarding activity, such as exhibited by the compounds of the invention, could be used to control unwanted growth of ornamental trees and shrubbery. Another application of compounds of the invention would be that of stopping or retarding sugar cane growth and reducing early senescence.

Meristematic activity of the compounds of this invention, and particularly the compound prepared in Example I, was observed at rates as low as 0.5 pound per acre of postemergence application although a 1.0 pound per acre rate of application has thus far provided a more satisfactory long-term growth retardation effect. The precise rate of application of a compound or compounds of this invention, in order to attain the desired extent of meristematic activity, will of course vary and would depend on a variety of factors such as, for example, climatic conditions, soil conditions, method of application, resistance of a particular plant species or the like, all of which parameters may be readily determined by straight-forward laboratory or field testing in a manner known to the art.

Of course, the compounds of this invention may be used as such or in formulation with agronomically acceptable adjuvants, inert carriers, pesticides, stabilizers, safeners, fertilizers, herbicides and the like. The compounds of this invention whether or not in formulation with the other agronomically acceptable materials may be applied in the form of dusts, granules, wettable powders, solutions, suspensions, aerosols, emulsions, dispersions or the like in a manner well known to the art. When formulated with other typically used agronomically acceptable materials, the amount of compound or compounds of this invention may vary over a wide range, for example, from about 0.05 to about 95 percent and typically from about 5 to about 75 percent by weight on weight of formulation.

Although the invention has been described in considerable detail with reference to illustrative embodiments thereof, it is to be understood that many variations may be made therein, by those skilled in the art without departing from the spirit and scope of the invention, except insofar as the same is defined by the appended claims.

We claim:

1. A compound, having plant growth regulating properties, represented by the formula:

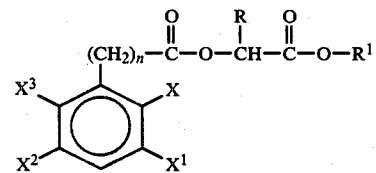

wherein,

X is halogen;

$X^1$ is hydrogen, nitro, or

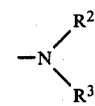

wherein $R^2$ and $R^3$ are the same or different and represent hydrogen, $C_1$ to $C_4$ alkyl, alkoxy or haloalkyl or

wherein $R^4$ is $C_1$ to $C_4$ alkyl;

$X^2$ is halogen;

$X^3$ is hydrogen, nitro, amino, or $C_1$ to $C_4$ alkyl, alkoxy or haloalkyl, provided that either $X^1$ or $X^3$ is other than hydrogen;

R is hydrogen or $C_1$ to $C_4$ alkyl;

$R^1$ is hydrogen, $C_1$ to $C_{10}$ alkyl, haloalkyl or alkoxyalkyl, or an agronomically acceptable ionic species; and n is 0 or 1.

2. A compound of claim 1 wherein X and $X^2$ are chlorine, $X^1$ is hydrogen and $X^3$ is alkoxy.

3. A compound of claim 1 wherein X and $X^2$ are halogen, $X^3$ is hydrogen and $X^1$ is

4. A compound of claim 3 wherein $R^2$ is hydrogen and $R^3$ is

5. A compound of claim 1 which is 2,5-dichloro-6-methoxybenzoic acid, (ethoxycarbonyl)ethyl ester.

6. In a method of regulating plant growth wherein a growth regulating amount of a plant growth regulating agent is applied to the plant wherein the improvement resides in using as the plant growth regulating agent a compound or mixture of compounds as defined in claim 1.

7. The improvement of claim 6 wherein the plant growth regulating agent is 2,5-dichloro-6-methoxybenzoic acid, (ethoxycarbonyl)ethyl ester.

* * * * *